United States Patent [19]

Hoek et al.

[11] Patent Number: 4,499,209

[45] Date of Patent: Feb. 12, 1985

[54] PROCESS FOR THE PREPARATION OF A FISCHER-TROPSCH CATALYST AND PREPARATION OF HYDROCARBONS FROM SYNGAS

[75] Inventors: Arend Hoek; Martin F. M. Post; Johannes K. Minderhoud; Peter W. Lednor, all of Amsterdam, Netherlands

[73] Assignee: Shell Oil Company, Houston, Tex.

[21] Appl. No.: 546,670

[22] Filed: Oct. 28, 1983

[30] Foreign Application Priority Data

Nov. 22, 1982 [NL] Netherlands .......................... 8204525

[51] Int. Cl.³ .............................................. C07C 1/04
[52] U.S. Cl. ..................................... 518/707; 518/703; 518/704; 518/714; 518/715; 585/310; 585/319; 585/322; 585/408; 585/638; 585/469; 502/242
[58] Field of Search ............... 518/707, 706, 715, 714; 585/310, 319, 322, 408, 469, 638

[56] References Cited

U.S. PATENT DOCUMENTS

| | | | |
|---|---|---|---|
| 2,594,301 | 4/1952 | Eastman et al. | 518/711 |
| 4,337,176 | 6/1982 | Boersma et al. | 518/713 |
| 4,338,089 | 7/1982 | Schaper et al. | 518/714 |
| 4,385,193 | 5/1983 | Bijwaard et al. | 518/715 |

*Primary Examiner*—Howard T. Mars

[57] ABSTRACT

A Fischer-Tropsch catalyst is prepared by impregnating a silica carrier with a solution of a zirconium or titanium compound, calcining the composition thus obtained, thereafter impregnating the carrier with a cobalt compound-containing solution and calcining and reducing the composition thus obtained. Catalysts so prepared and containing 5–40 pbw of cobalt and 2–150 pbw of zirconium or titanium per 100 pbw of silica, are used in the preparation of hydrocarbons from a $H_2/CO$ mixture.

13 Claims, No Drawings

PROCESS FOR THE PREPARATION OF A FISCHER-TROPSCH CATALYST AND PREPARATION OF HYDROCARBONS FROM SYNGAS

BACKGROUND OF THE INVENTION

The invention relates to a process for the preparation of a Fischer-Tropsch catalyst which contains cobalt, zirconium or titanium, and silica. It relates further to the use of such a catalyst in the preparation of hydrocarbons by reaction of carbon monoxide with hydrogen.

The preparation of hydrocarbons from a $H_2/CO$ mixture by contacting this mixture at elevated temperature and pressure with a catalyst is known in the literature as Fischer-Tropsch hydrocarbon synthesis. Catalysts often used for this purpose contain iron or cobalt together with one or more promoters and/or a carrier material. The conventional techniques of preparing Fischer-Tropsch catalysts are the precipitation route, the melting route and the impregnation route. Of these techniques the impregnation route is much to be preferred since this route is not so costly and/or time consuming, produces better reproducible results and generally yields materials with better catalytic properties. Briefly, the impregnation route involves contacting a porous carrier once or several times with an aqueous solution containing an iron or cobalt compound and, if desired, one or more compounds of the appropriate promoters, followed by removal of the liquid and calcination and reduction of the composition obtained.

The composition of the product obtained in the Fischer-Tropsch hydrocarbon synthesis by using catalysts prepared by impregnation is largely dependent on the catalytically active metal which is present on the catalyst. The use of a cobalt catalyst prepared by impregnation results in a product which consists mainly of unbranched paraffins. The use of an iron catalyst prepared by impregnation results in a product which, in addition to unbranched paraffins, contains a considerable quantity of olefins and oxygen-containing organic compounds. With a view to the composition of the product obtained, for the preparation of products suitable for use as motor fuels, preference is given to the use of a cobalt catalyst.

Earlier investigations have shown that catalysts prepared by impregnation of a silica carrier with an aqueous solution of a cobalt salt followed by calcination and reduction of the composition obtained showed excellent $C_3{}^+$ and $C_5{}^+$ selectivity but only relatively low activity. By including in the aqueous solution with which the silica was impregnated a zirconium or titanium salt in addition to the cobalt salt, the activity of the catalysts could be roughly doubled without loss of the aforementioned high $C_3{}^+$ and $C_5{}^+$ selectivity. A remarkable feature of these catalysts prepared by co-impregnation with the aid of an aqueous solution is the extremely narrow range of promoter load levels within which the promoter exercises its activity-promoting effect on the catalyst. It was found that, whereas for these catalysts the inclusion of a quantity of about 1 pbw of zirconium per 100 pbw of silica led to, roughly, doubling of their activity, the inclusion of larger quantities of zirconium caused a rapid decrease of activity promotion and, upon inclusion of a quantity of about 6 pbw per 100 pbw of silica, the activity-promoting affect was seen to have disappeared altogether. In the latter case a catalyst was obtained which had an activity almost equal to that of a catalyst containing nothing but cobalt.

Although the catalysts prepared by co-impregnation with the aid of an aqueous solution as described hereinbefore have acceptable activity, there is an unmistakable need for catalysts of this type having higher activity.

Continued investigation into this subject was carried out to determine whether changes in the technique of impregnation might lead to widening of the range within which the promoter exercises its activity-promoting effect on the catalyst. For this purpose replacement of the co-impregnation by separate impregnation was investigated in the first place. Catalysts were prepared by impregnating a silica carrier first with an aqueous solution of a cobalt compound and subsequently, after calcination of the cobalt-containing composition, impregnating the latter with an aqueous solution of a zirconium compound, followed by calcination and reduction of the zirconium and cobalt-containing composition. Thus were prepared catalysts containing different quantities of zirconium. It was found that just as in the case of the catalysts prepared by co-impregnation, so in the case of the catalysts prepared by separate impregnation did the incorporation of a quantity of about 1 pbw zirconium per 100 pbw of silica result in—roughly—doubled activity. In the catalysts prepared by separate impregnation the range within which the promoter exercises its activity-promoting effect on the catalyst was found to have decreased in comparison with the catalysts prepared by co-impregnation. Whereas in the catalysts prepared by co-impregnation the incorporation of about 6 pbw of zirconium per 100 pbw of silica resulted in an activity level corresponding to that of a catalyst containing nothing but cobalt, the catalysts prepared by separate impregnation containing about 6 pbw of zirconium per 100 pbw of silica were seen to be entirely inactive.

On the assumption that in the above-mentioned separate impregnation the use of an organic promoter compound dissolved in an organic solvent might lead to the purpose intended, catalysts were prepared by impregnating a silica carrier first with an aqueous solution of a cobalt compound and, after calcination of the cobalt-containing composition, impregnating the latter with a solution of an organic zirconium compound in an organic solvent, followed by calcination and reduction of the zirconium and cobalt-containing composition. Thus were prepared catalysts containing varying proportions of zirconium. It was found than when these catalysts were used for the preparation of hydrocarbons from $H_2/CO$ mixtures, they behaved in precisely the same manner as the aforementioned catalysts which had been prepared by separate impregnation using an aqueous solution of an inorganic zirconium compound, viz. catalysts containing about 1 pbw zirconium per 100 pbw silica showed roughly doubled activity, whereas catalysts containing about 6 pbw zirconium per 100 pbw silica proved to be entirely inactive.

The above-mentioned disappointing results as to the effect of a change in the impregnation method upon the activity of the promoted $Co/SiO_2$ catalysts notwithstanding, yet another attempt was made at achieving catalysts with improved activity by using the above-described separate impregnation, but with the order of the impregnation steps being reversed. This surprisingly led to the find that in this way it is possible to prepare promoted $Co/SiO_2$ catalyts whose activity is 3–4 times as high as that of a catalyst containing nothing but cobalt. In order to achieve an improvement in activity which exceeds that which can be achieved by co-impregnation of the promoter together with the cobalt or the separate impregnation of the promoter after the cobalt, the proportion of promoter deposited on the silica prior to the cobalt should be at least 2 pbw per 100 pbw silica for catalysts containing 5-40 pbw cobalt per 100 pbw silica. Contrary to what is seen for the catalysts in which the promoter has been deposited on the carrier by co-impregnation together with the cobalt or by separate impregnation of the promoter after the cobalt, the range of promoter loads within which the promoter exercises its activity-promoting effect is very wide in the case of the catalysts in which the promoter is deposited on the carrier previous to the cobalt. In principle, when preparing these catalysts promoter quantities of up to a maximum of 150 pbw per 100 pbw silica may be considered.

SUMMARY OF THE INVENTION

The present invention therefore relates to a process for the preparation of a Fischer-Tropsch catalyst which contains cobalt, zirconium or titanium, and silica, which process comprises impregnating a silica carrier with a solution of a zirconium or titanium compound, calcining the composition thus obtained, impgregnating the calcined composition with a solution of a cobalt compound, and calcining and reducing the composition thus obtained.

The present patent application also relates to a process for the preparation of hydrocarbons by catalytic reaction of carbon monoxide with hydrogen, in which a $H_2$ and CO-containing feed is contacted at elevated temperature and pressure with a catalyst which comprises 5-40 pbw of cobalt and 2-150 pbw of zirconium or titanium per 100 pbw of silica and which has been prepared by impregnating a silica carrier once or several times with a solution of a zirconium or titanium compound, calcining the composition thus obtained, impregnating the calcined composition once or several times with a solution of a cobalt compound and calcining and reducing the composition thus obtained.

DETAILED DESCRIPTION OF THE INVENTION

The catalyst according to the invention is prepared by separate impregnation, with first the promoter having been deposited on the carrier and subsequently the cobalt. The separate impregnation steps may be carried out in the form of dry or wet impregnation. In case of dry impregnation the carrier material is contacted with a solution containing a compound of the metal to be impregnated, which solution has a volume substantially corresponding with the pore volume of the carrier material. In case of wet impregnation the carrier material is contacted with a solution containing a compound of the metal to be impregnated, which solution has a volume substantially more than twice the pore volume of the carrier material. In the process according to the invention preference is given to the use of catalysts during the preparation of which the separate impregnation steps have been carried out in the form of dry impregnation. The number of impregnation steps to be carried out during the production of the catalysts is determined substantially by the degree of solubility of the metal compounds in the solvent used and the desired metal load on the catalyst, with the understanding that more impregnation steps will be needed according as the degree of solubility of the metal compounds in the solvent used is lower and the desired metal load on the catalyst is higher.

After the last impregnation step in which the promoter is deposited on the silica and after the last impregnation step in which the cobalt is deposited on the silica the metal-containing composition obtained should be calcined. If the deposition of the promoter and/or the cobalt is carried out in more than one step, the metal-containing composition obtained is preferably dried and calcined after each impregnation step.

The calcination is preferably carried out at a temperature between 350° and 700° C. After the calcination succeeding to the last impregnation step in which the cobalt is deposited on the silica, the composition should be reduced. This reduction is preferably carried out at a temperature between 200° and 350° C.

The catalysts preferably used in the process according to the invention are catalysts containing zirconium as a promoter. For impregnating the silica with the promoter and the cobalt both aqueous and non-aqueous solutions are eligible. Examples of suitable aqueous solutions of zirconium compounds are solutions of zirconium nitrate or zirconyl chloride in water. Examples of suitable non-aqueous solutions of zirconium compounds are solutions of zirconium alkoxides in aromatic hydrocarbons or in mixtures of aromatic hydrocarbons and aliphatic alcohols. An impregnation liquid which is very suitable for the present purpose is a solution of zirconium tetrapropoxide in a mixture of benzene and propanol. In view of the relatively low degree of solubility in water of most of the inorganic zirconium compounds and the preferred use of catalysts with a relatively high zirconium load, the present catalysts are preferably prepared by using a solution of an organic zirconium compound in an organic solvent or a mixture of organic solvents as the impregnation liquid for depositing the zirconium on the silica. The deposition of the cobalt on the silica is preferably carried out by using an aqueous solution of a cobalt compound as the impregnation liquid. Cobalt compounds suitable for this purpose are cobalt nitrate, cobalt carbonate, cobalt chloride and cobalt sulfate.

Catalysts according to the invention preferably contain 5-40 pbw cobalt and 2-150 pbw zirconium or titanium per 100 pbw silica. Even more preference is given to catalysts containing at most 100 pbw and in particular at most 20 pbw of promoter per 100 pbw of silica. Such catalysts preferably contain zirconium as a promoter.

The present patent application further relates to a process for the preparation of hydrocarbons by catalytic reaction of carbon monoxide with hydrogen, in which a $H_2$ and CO-containing feed is contacted at elevated temperature and pressure with a catalyst which comprises 5-40 pbw of cobalt and 2-150 pbw of zirconium or titanium per 100 pbw of silica and which has been prepared by impregnating a silica carrier with a solution of a zirconium or titanium compound, calcining the composition thus obtained, impregnating the calcined composition with a solution of a cobalt compound and calcining and reducing the composition thus obtained.

This process is preferably carried out at a temperature of 125°-350° C. and in particular of 175°-275° C. and a pressure of 5-150 bar and in particular 10-100 bar. The starting material is a $H_2$ and CO-containing feed which preferably has a $H_2/CO$ molar ratio higher than 1.75.

The hydrocarbon preparation according to the invention may very suitably be carried out as an independent process in which $H_2$ and CO-containing feed is converted in one step into a hydrocarbon mixture. A very suitable feed in this case is a $H_2/CO$ mixture obtained by steam gasification of a carbon-containing material, such as coal, by gasification, or from light hydrocarbons, such as natural gas, by steam reforming or partial oxidation.

The hydrocarbon preparation according to the invention may also very suitably be carried out as part of a multi-step process for the conversion of a $H_2$ and CO-containing feed. In this case there are three possibilites, viz.:

(A) The process is used as the second step of a two-step process.
(B) The process is used as the first step of a two-step process.
(C) A combination of the processes mentioned under (A) and (B), with the process according to the invention being used as the second step of a three-step process.

Each one of these multi-step processes will be further explained hereinafter.

In the process mentioned under (A) a $H_2/CO$ mixture is contacted in the first step with a catalyst containing one or more metal components having catalytic activity for the conversion of a $H_2/CO$ mixture into hydrocarbons and/or oxygen-containing organic compounds and unconverted hydrogen and carbon monoxide present in the reaction product of the first step—together with other components of that reaction product, if desired—are used as the feed for the hydrocarbon preparation according to the invention. Depending on the nature of the catalyst chosen in the first step, either substantially aromatic hydrocarbons, or substantially paraffinic hydrocarbons, or substantially oxygen-containing organic compounds may be prepared in this step.

If it is the object in the first step to prepare substantially aromatic hydrocarbons, then use may quite suitably be made of a catalyst mixture containing either a methanol or dimethyl ether synthesis catalyst or a $Fe/Mg/Al_2O_3$ or $Fe/Cr/SiO_2$ catalyst prepared by impregnation together with a crystalline metal silicate which is characterized in that after one hour's calcination in air at 500° C. it has the following properties:

(a) an X-ray powder diffraction pattern in which the strongest lines are the lines mentioned in Table A.

TABLE A

| d(Å) |
| --- |
| 11.1 ± 0.2 |
| 10.0 ± 0.2 |
| 3.84 ± 0.07 |
| 3.72 ± 0.06, and |

(b) in the formula which represents the composition of the silicate expressed in moles of the oxides and in which, in addition to $SiO_2$, one or more oxides of a trivalent metal M, chosen from the group formed by aluminum, iron, gallium, rhodium, chromium, and scandium are present, the $SiO_2/M_2O_3$ molar ratio is higher than 10.

If it is the object in the first step of the two-step process mentioned under (A) to prepare substantially paraffinic hydrocarbons, then use may very suitably be made of the above-mentioned $Fe/Mg/Al_2O_3$ or $Fe/Cr/SiO_2$ catalysts prepared by impregnation. If the first step of the two-step process mentioned under (A) is carried out with the object of preparing oxygen-containing organic compounds, then use may very suitably be made of a methanol or dimethyl ether synthesis catalyst. Methanol synthesis catalysts suitable for use in the first step of the two-step process mentioned under (A) are $ZnO/Cr_2O_3$ and $Cu/ZnO/Cr_2O_3$ catalysts. A dimethyl ether synthesis catalyst suitable for use in the first step of the two-step process mentioned under (A) is a mixture of gamma —$Al_2O_3$ and the $Cu/ZnO/Cr_2O_3$ methanol synthesis catalyst mentioned hereinbefore.

In the two-step process mentioned under (B) as well as in the three-step process mentioned under (C) the fact is utilized that the high-boiling part of the product obtained in the hydrocarbon preparation according to the invention can be converted in a high yield into middle distillates using a catalytic hydrotreatment. In the present patent application the term "middle distillates" is used to designate hydrocarbon mixtures whose boiling range corresponds substantially with that of the kerosene and gas oil fraction obtained in the conventional atmospheric distillation of crude mineral oil. Said distillation is used to separate from crude mineral oil one or more gasoline fractions having a boiling range between 30° and 200° C., one or more kerosene fractions having a boiling range between 140° and 300° C. and one or more gas oil fractions having a boiling range between 180° and 370° C., successively.

The two-step process mentioned under (B) comprises carrying out the process according to the invention as the first step, followed by a catalytic hydrotreatment as the second step. The three-step process mentioned under (C) comprises carrying out the two-step process mentioned under (A), with the hydrocarbon preparation according to the invention forming the second step, followed by a catalytic hydrotreatment as the third step. The feed chosen for the catalytic hydrotreatment is at least the part of the reaction product of the hydrocarbon preparation according to the invention whose initial boiling point lies above the final boiling point of the heaviest middle distillate desired as final product. The hydrotreatment which is characterized by a very low hydrogen consumption yields middle distillates with considerably lower pour points than those obtained in the direct Fischer-Tropsch conversion of a $H_2/CO$ mixture. Catalysts very suitable for carrying out the catalytic hydrotreatment are those containing one or more noble metals of Group VIII supported on a carrier, and particularly suitable is a catalyst containing platinum supported on a carrier 13–15% w of which consists of alumina, the rest of silica.

The invention is now illustrated with the aid of the following example.

EXAMPLE

18 Catalysts (catalysts 1–18) were prepared. Catalyst 1 contained 25 pbw cobalt per 100 pbw silica. Catalysts 2–18, in addition to 25 pbw cobalt per 100 pbw silica, contained varying quantities of zirconium. All the catalysts were prepared by dry impregnation of the same silica carrier. After each impregnation step the compositions obtained were dried at 120° C. and calcined in air at 500° C. After the last calcination step the compositions were reduced in hydrogen at 250° C. Further information concerning the preparation of the catalysts is given hereinafter.

Catalyst 1

One-step impregnation of the silica carrier with an aqueous solution of cobalt nitrate.

Catalysts 2 and 3

One-step impregnation of the silica carrier with an aqueous solution containing both cobalt nitrate and zirconium nitrate. Per 100 pbw silica catalysts 2 and 3 contained 0.9 and 6 pbw zirconium, respectively.

Catalysts 4–8

Impregnation of the silica carrier, first in one step with an aqueous solution of cobalt nitrate and then in one step with an aqueous solution of zirconium nitrate.

Per 100 pbw silica catalysts 4–8 contained 0.45, 0.9, 1.8, 3.6 and 6 pbw zirconium, respectively.

Catalysts 9 and 10

Impregnation of the silica carrier, first in one step with an aqueous solution of cobalt nitrate and then in one step with a solution of a zirconium tetrapropoxide in a mixture of propanol and benzene. Per 100 pbw silica catalysts 9 and 10 contained 0.9 and 6 pbw zirconium, respectively.

Catalysts 11 and 12

Impregnation of the silica carrier, first in one step with an aqueous solution of zirconium nitrate and then in one step with an aqueous solution of cobalt nitrate. Per 100 pbw silica catalysts 11 and 12 contained 0.9 and 6 pbw zirconium, respectively.

Catalysts 13–18

One-step or multi-step impregnation of the silica carrier with a solution of zirconium tetrapropoxide in a mixture of propanol and benzene and then impregnation in one step with an aqueous solution of cobalt nitrate. In the preparation of catalysts 13–18 the impregnation of the silica carrier with the zirconium tetrapropoxide solution was carried out in one, one, two, three, four and eight steps, respectively. Per 100 pbw silica catalysts 13–18 contained 0.9, 6, 12, 18, 45 and 163 pbw zirconium, respectively.

The cobalt loads and surface areas of the catalysts 2–18 are given in Table B.

Of catalysts 1–18 described hereinbefore only catalysts 12 and 14–17 are suitable for use in the process according to the invention. The other catalysts fall outside the scope of the invention. They have been included in the patent application for comparison.

Catalysts 1–18 were tested in twenty experiments (experiments 1–20) in the preparation of hydrocarbons from mixtures of carbon monoxide and hydrogen. The experiments were carried out in 50 ml reactor containing a fixed catalyst bed of 7.5 ml volume.

The conditions used for carrying out the experiments and the results of the experiments are given in Table C.

TABLE B

| Catalyst No. | 2 | 3 | 4 | 5 | 6 | 7 | 8 | 9 | 10 | 11 | 12 | 13 | 14 | 15 | 16 | 17 | 18 |
|---|---|---|---|---|---|---|---|---|---|---|---|---|---|---|---|---|---|
| Cobalt load, mg cobalt per ml catalyst | 106 | 107 | 104 | 103 | 107 | 106 | 106 | 104 | 106 | 105 | 107 | 112 | 105 | 106 | 105 | 102 | 94 |
| Surface area, m² per ml catalyst | 31 | 30 | 31 | 31 | 30 | 29 | 29 | 31 | 28 | 28 | 24 | 30 | 30 | 29 | 28 | 24 | 14 |

TABLE C

| Experiment No. | 1 | 2 | 3 | 4 | 5 | 6 | 7 | 8 | 9 | 10 | 11 | 12 | 13 | 14 | 15 | 16 | 17 | 18 | 19 | 20 |
|---|---|---|---|---|---|---|---|---|---|---|---|---|---|---|---|---|---|---|---|---|
| Catalyst No. | 1 | 2 | 3 | 4 | 5 | 6 | 7 | 8 | 9 | 10 | 11 | 12 | 13 | 14 | 15 | 16 | 17 | 18 | 16 | 16 |
| Temperature, °C. | ← | ← | ← | ← | ← | ← | ← | ← | 205 | → | → | → | → | → | → | → | → | → | 220 | 220 |
| Pressure, bar | ← | ← | ← | ← | ← | ← | ← | ← | 20 | → | → | → | → | → | → | → | → | → | → | → |
| Space velocity $l.l^{-1}.h^{-1}$ | ← | ← | ← | ← | ← | ← | ← | ← | 2000 | → | → | → | → | → | → | → | → | → | 3000 | 1500 |
| $H_2/CO$ molar ratio of feed | ← | ← | ← | ← | ← | ← | ← | ← | 3 | → | → | → | → | → | → | → | → | → | → | 2 |
| CO conversion, % v | 21 | 45 | 23 | 35 | 43 | 38 | 9 | — | 44 | — | 40 | 55 | 42 | 62 | 67 | 71 | 70 | 13 | 77 | 85 |
| $C_3^+$ selectivity calculated on $C_1^+$, % w | ← | ← | ← | ← | ← | ← | ← | ← | 87+ | → | → | → | → | → | → | → | → | → | 75 | 93 |
| $C_5^+$ selectivity calculated on $C_1^+$, % w | ← | ← | ← | ← | ← | ← | ← | ← | 80+ | → | → | → | → | → | → | → | → | → | 66 | 88 |

TABLE D

| Composition, % w | $C_1^+$ product of Experiment 15 | $C_5^+$ fraction of the $C_1^+$ product of Experiment 15 | $C_1^+$ product after the catalytic hydrotreatment |
|---|---|---|---|
| $C_4^-$ | 20 | — | 2 |
| $C_5$-150° C. | 14 | 17 | 20 |
| 150–250° C. | 17 | 21 | 28 |
| 250–360° C. | 20 | 25 | 35 |
| 360–400° C. | 6 | 8 | 7 |
| 400° C.+ | 23 | 29 | 8 |

Of the experiments listed in Table C only Experiments 12, 14–17, 19 and 20 are experiments according to the invention. In these experiments $Co/Zr/SiO_2$ catalysts were used which contained 25 pbw cobalt and 6–45 pbw zirconium per 100 pbw silica and had been prepared by impregnating a silica carrier first with zirconium and then with cobalt. All these catalysts showed high activity. The other experiments fall outside the scope of the invention. They have been included in the patent application for comparison. In Experiment 1 a catalyst containing no zirconium was used. In Experiments 2 and 3 $Co/Zr/SiO_2$ catalysts prepared by co-impregnation were used. In Experiments 4–10 catalysts were used which had been prepared by impregnation carried out step-wise, but with first the cobalt and subsequently the zirconium being deposited on the silica. In Experiments 11, 13 and 18 catalysts were used which, although they had been prepared by impregnation carried out step-wise in the correct order of steps (first zirconium, then cobalt), contained less than 2 or more than 150 pbw zirconium per 100 pbw silica. All the catalysts used in the comparative experiments showed relatively low to very low activity and in two cases no activity at all.

Catalytic hydrotreatment

An Experiment 21 was carried out in which the $C_5+$ fraction of the product obtained according to Experiment 15 was passed together with hydrogen through a 50-ml reactor containing a fixed catalyst bed, at a temperature of 345° C., a pressure of 130 bar, a space velocity of 1.25 $1.1^{-1}.h^{-1}$ and a hydrogen/oil ratio of $2000 N1.1^{-1}$. The catalyst was a $Pt/SiO_2—Al_2O_3$ catalyst containing 0.82 parts by weight platinum per 100 pbw of carrier, which carrier consisted of 14.6% by weight of alumina and 85.4% by weight of silica. The results of Experiment 21 are given in Table D.

From the results given in Table D it appears that when a catalytic hydrotreatment is applied to a product prepared according to the invention, a considerable part of the 400° C.+ fraction is converted (a decrease from 29 to 8%w) and a considerable quantity of 150°–360° C. fraction is formed (an increase from 46 to 63%w), whereas only very little 150° C.− fraction is formed (an increase from 17 to 22%w).

What is claimed is:

1. A process for the preparation of hydrocarbons by catalytic reaction of carbon monoxide with hydrogen, characterized in that a $H_2$ and CO-containing feed is contacted at a temperature of 125°–350° C. and a pressure of 5–150 bar with a catalyst which contains 5–40 pbw cobalt and 2–150 pbw zirconium or titanium per 100 pbw silica and has been prepared by impregnating a silica carrier once or several times with a solution of a zirconium or titanium compound, calcining the composition thus obtained, impregnating the calcined composition once or several times with a solution of a cobalt compound and calcining and reducing the compositions thus obtained.

2. A process as claimed in claim 1, characterized in that the impregnation steps for the preparation of the catalyst are carried out as dry impregnation.

3. A process as claimed in claim 1, characterized in that if the deposition of zirconium or titanium and/or cobalt is carried out in more than one step the metal-containing compositions obtained are calcined after each impregnation step.

4. A process as claimed in claim 1, characterized in that the calcination of the metal-containing compositions is carried out at a temperature of 350°–700° C. and that the reduction of the metal-containing compositions is carried out at a temperature of 200°–350° C.

5. A process as claimed in claim 1, characterized in that the catalyst contains zirconium as a promoter.

6. A process as claimed in claim 1, characterized in that for depositing zirconium on the silica a solution of an organic zirconium compound in an organic solvent or mixtures of organic solvents is used as the impregnation liquid.

7. A process as claimed in claim 1, characterized in that the catalyst comprises at most 100 pbw of zirconium or titanium per 100 pbw of silica.

8. A process as claimed in claim 7, characterized in that the catalyst contains at most 20 pbw of zirconium or titanium per 100 pbw of silica.

9. A process as claimed in claim 1, characterized in that it is carried out at a temperature of 175°–275° C. and a pressure of 10–100 bar.

10. A process as claimed in claim 1, characterized in that it is applied to a $H_2$ and CO-containing feed having a $H_2/CO$ molar ratio higher than 1.75.

11. A process as claimed in claim 1, characterized in that it is used as part of a multi-step process for the conversion of a $H_2$ and CO-containing feed.

12. A process as claimed in claim 11, characterized in that it is used as the second step of a two-step process in which a $H_2/CO$ mixture is contacted in the first step with a catalyst containing one or more metal components with catalytic activity for converting a $H_2/CO$ mixture into hydrocarbons and/or oxygen-containing organic compounds and in which $H_2$ and CO present in the reaction product of the first step—optionally together with other components of that reaction product—are used as the feed for the second step.

13. A process as claimed in claim 11, characterized in that it is used as the first step of a two-step process for preparing middle distillates from a $H_2$ and CO-containing feed, in which at least the part of the reaction product of the first step whose initial boiling point lies above the final boiling point of the heaviest middle distillate desired as end-product is subjected in the second step to a catalytic hydrotreatment.

* * * * *